US00PP25272P3

(12) United States Plant Patent
Knott et al.

(10) Patent No.: US PP25,272 P3
(45) Date of Patent: Jan. 27, 2015

(54) SMOOTH CORDGRASS NAMED 'LA11-103'

(50) Latin Name: ***Spartina alterniflora* Loisel.**
Varietal Denomination: LA11-103

(71) Applicants: Carrie Ann Knott, Baton Rouge, LA (US); Michael David Materne, Baton Rouge, LA (US); Herry Sutjahjo Utomo, Rayne, LA (US); Prasanta Kumar Subudhi, Baton Rouge, LA (US); Niranjan Baisakh, Baton Rouge, LA (US); Stephen Alan Harrison, Baton Rouge, LA (US)

(72) Inventors: Carrie Ann Knott, Baton Rouge, LA (US); Michael David Materne, Baton Rouge, LA (US); Herry Sutjahjo Utomo, Rayne, LA (US); Prasanta Kumar Subudhi, Baton Rouge, LA (US); Niranjan Baisakh, Baton Rouge, LA (US); Stephen Alan Harrison, Baton Rouge, LA (US)

(73) Assignee: Board of Supervisors of Louisiana State University and A&M College Through The LSU Ag Center, Baton Rouge, LA (US)

( * ) Notice: Subject to any disclaimer, the term of this patent is extended or adjusted under 35 U.S.C. 154(b) by 169 days.

(21) Appl. No.: 13/507,357

(22) Filed: Sep. 20, 2012

(65) Prior Publication Data

US 2014/0082802 P1 Mar. 20, 2014

(51) Int. Cl.
*A01H 5/00* (2006.01)

(52) U.S. Cl.
USPC ..... Plt./387

(58) Field of Classification Search
USPC ..... Plt./384, 387
See application file for complete search history.

*Primary Examiner* — Annette Para
(74) *Attorney, Agent, or Firm* — James C. Carver

(57) ABSTRACT

A new variety of smooth cordgrass identified as 'LA11-103' is disclosed as being genetically different from 'Vermilion', 'LA11-101', and 'LA11-102', as having rapid establishment and growth in natural brackish and saline marsh environments, and excellent seed set and germination.

2 Drawing Sheets

The development of this invention was partially funded with Hatch Act Formula Funds (Project number LAB93864) and through grants from the United States Department of Agriculture's National Institute of Food and Agriculture (Agreement numbers: 2010-34396-21191, 2009-34396-20051, 2008-34396-19316, 2006-34396-17624, 2005-34396-16498). The Government may have certain rights in this invention.

This invention pertains to a new and distinct variety of smooth cordgrass.

BACKGROUND OF THE INVENTION

Smooth cordgrass (*Spartina alterniflora* Loisel.) is a perennial grass native to intertidal saline marshes along the Atlantic and Gulf of Mexico coasts in the United States. It is used in numerous restoration projects to decrease coastal erosion. In Louisiana, one smooth cordgrass variety, 'Vermilion' (unpatented), is used extensively. The widespread use of a single variety reduces genetic variation, thus reducing the ability to adapt to environmental changes. 'LA11-103', along with 'LA11-101' (U.S. Plant patent application Ser. No. 13/507,358)and 'LA11-102' (U.S. Plant patent application Ser. No. 13/507,345), were invented to provide genetically diverse smooth cordgrass varieties for northern Gulf of Mexico restoration projects.

Smooth cordgrass seeds were collected from one hundred twenty-six (126) smooth cordgrass populations throughout Louisiana in 1998. Preliminary work, which preceded this invention, evaluated smooth cordgrass plant survival and vigor in natural marsh environments and freshwater production ponds (Ryan, 2003. utils.louislibraries.org/cgi-bin/lz0050.x?sitecode=LALUelib?http://etd.lsu.edu/docs/available/etd-1110103-133154/ and Ryan et al., *Journal of Aquatic Plant Management*, 45:90-99, 2007). In the preliminary work, no efforts were made to asexually reproduce 'LA11-103' for any purpose other than to provide plant material for plant performance evaluations. The new smooth cordgrass varieties ('LA11-101', 'LA11-102', and 'LA11-103') were designated as varieties and reproduced asexually beginning in 2010. 'LA11-103' has a unique and stable genotype, as determined by molecular marker profiles.

BRIEF SUMMARY OF INVENTION

Genus and Species Name

'LA11-103' is a new smooth cordgrass (*Spartina alterniflora* Loisel.) variety that is genetically different from 'Vermilion' and two additional new smooth cordgrass varieties, 'LA11-101' and 'LA11-102'. Genetic diversity was determined using thirteen molecular markers. 'LA11-103' is more vigorous one month after transplant than 'Vermilion' and produces more seeds that germinate than 'Vermilion'. 'LA11-103' is recommended for brackish and saline marsh restoration projects in the northern Gulf of Mexico, especially Louisiana, where genetically different smooth cordgrass varieties that rapidly establish and produce viable seeds are desired.

Variety Denomination

This new and distinct cordgrass variety, identified as 'LA11-103', is characterized by its unique genetic profile, as determined by thirteen (13) molecular markers, ability to recover quickly in natural environments, and high viable seed yields.

BRIEF DESCRIPTION OF THE DRAWINGS

The file of this Patent contains at least one photograph executed in color. Copies of this Patent or Patent Application with color drawings(s) will be provided by the US Patent and Trademark Office upon request and payment of the necessary fees.

DETAILED BOTANICAL DESCRIPTION

'LA11-103' was developed from seed collected from smooth cordgrass plants growing along the Barataria Waterway in Jefferson Parish La. (29° 34' 33.90" N.; 90° 3' 24.32" W.) in December of 1998. Collected seeds were germinated in a greenhouse at Baton Rouge, La. This population was selected in a phenotypic selection program because of high seed germination rates, seedling survival, and seedling vigor. The twenty (20) most vigorous seedlings from this population were selected in a second selection cycle and evaluated at Baton Rouge, La. In 1999, 'LA11-103', along with thirty-nine (39) additional genotypes, was selected in a third selection cycle. To provide plant material for continued experimental evaluations, rhizomes and stems of 'LA11-103' were harvested from the experimental plot at Baton Rouge and planted into containers in controlled greenhouses. This asexual reproduction was used solely to multiply the experimental line for evaluation, and not for the asexual reproduction of the variety.

Figure 1:
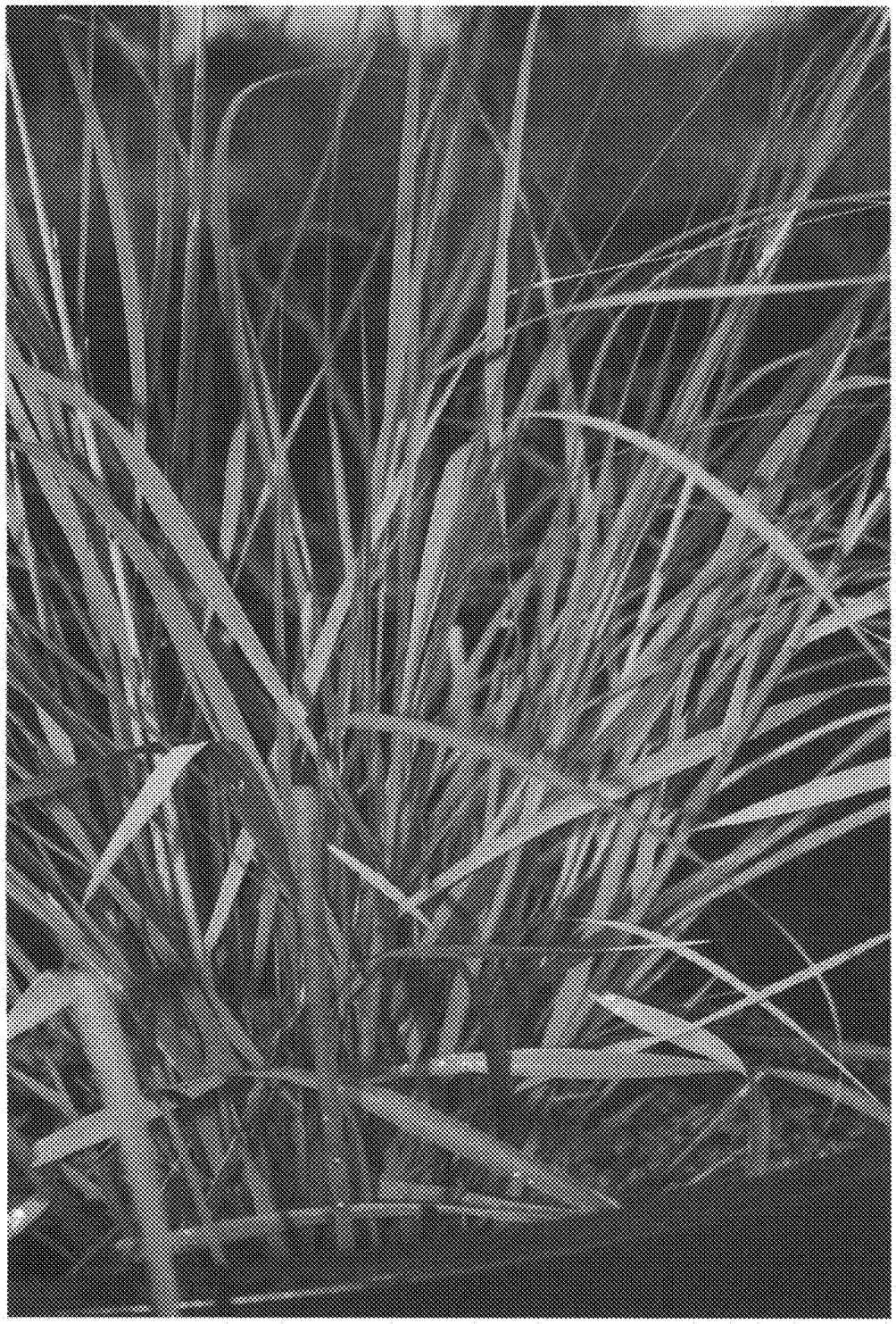
FIG. 1 is a color photograph of the novel smooth cordgrass variety identified as 'LA11-103' showing dark green leaves and red-purple stems at panicle emergence.
Figure 2:
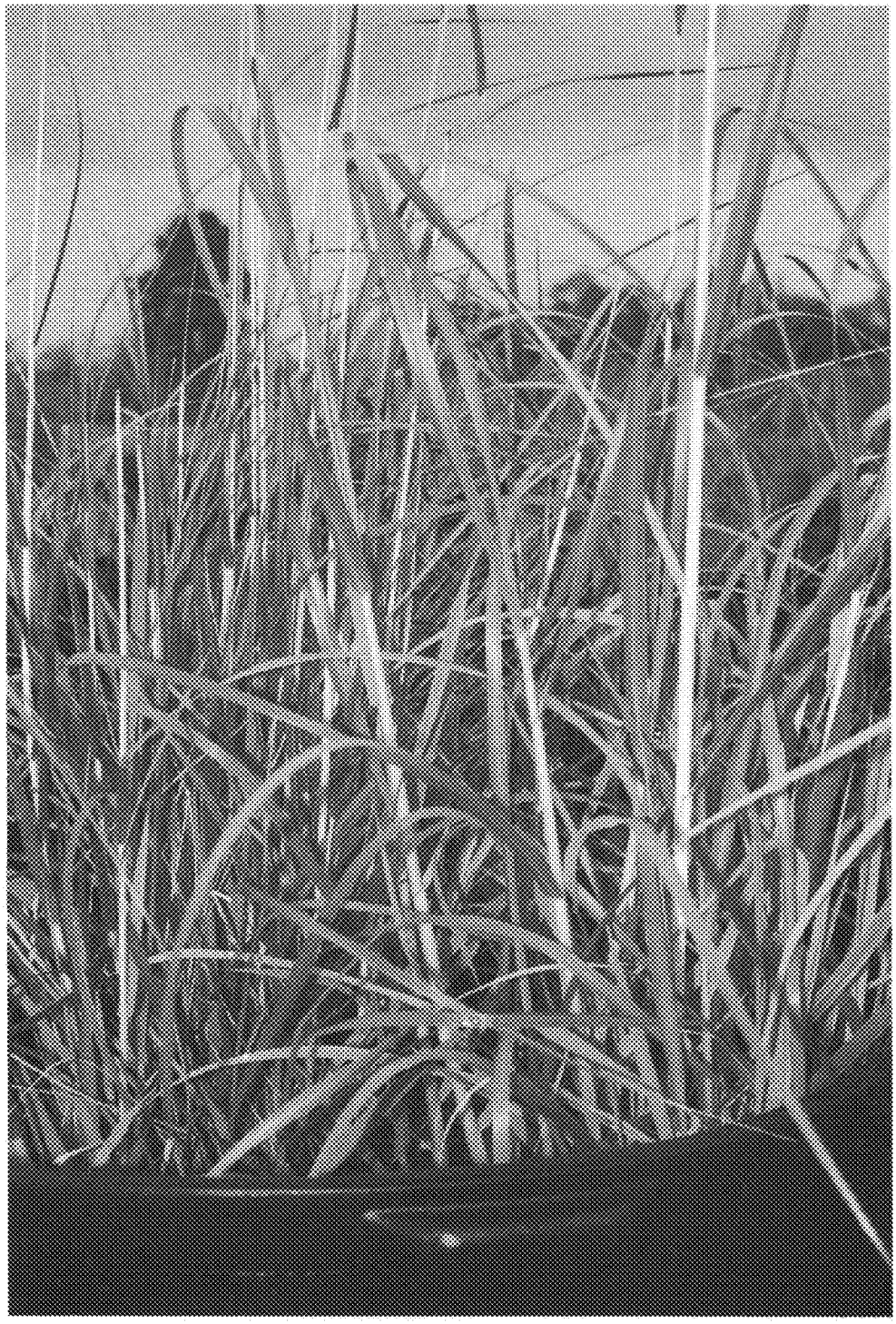
FIG. 2 is a color photograph of the smooth cordgrass variety identified as 'Vermilion' showing green leaves and pale green stems at panicle emergence.

The leaves of 'LA11-103' are slightly darker green [7.5 GY (5/4)] than 'Vermilion' [5 GY (5/4)] when color is determined with the MUNSELL® Book of Color (Munsell Color, Gretag Macbeth LLC, 617 Little Britain Road, New Windsor, N.Y. 12553-6148). 'LA11-103' stems are red-purple [5RP (5/6)], while 'Vermilion' stems are a pale green [2.5 GY (8/4)] beginning at panicle emergence (FIG. 1 and FIG. 2). 'LA11-103' is shorter than 'Vermilion', has a similar stem diameter, leaf width, panicle length, and panicle width as 'Vermilion' (Table A). However, physical characteristics can differ significantly from those described herein depending on growing conditions.

TABLE A

| Variety | Height† (cm) | Stem Diameter (mm) | Leaf Width (mm) | Panicle Length (cm) | Panicle Width (mm) |
|---|---|---|---|---|---|
| 'LA11-103' | 125.5 b | 6.9 b | 6.1 a | 22.2 a | 2.8 a |
| 'Vermilion | 148.8 a | 7.7 a | 6.6 a | 24.2 a | 2.6 a |

†Means within the same column that are followed by different letters are significantly different (t test, $p < 0.05$).

General description:

*Plant habit*.—Herbaceous grass with upright culms. Initially grows in a circular pattern. After 2-3 years of undisturbed growth, stands resemble 'donut' shape, where an outer ring of healthy culms continue to grow and the inner ring consists primarily of dead culms from previous years' growth.

*Culms*.—Round, hairless, and hollow. Spongy at the base. 'LA11-103' has culms similar in size to smooth cordgrass cv. 'Vermilion' about 10 mm above soil surface: average about 6.9 mm for 'LA11-103'. 'LA11-103' culms are reddish-purple [(5RP 5/6); (MUNSELL® Book of Color, Munsell Color Company, 1977, Gretag Macbeth LLC, 617 Little Britain Road, New Windsor, N.Y. 12553-6148)] beginning at panicle emergence.

*Plant height*.—In Southern Louisiana, 'LA11-103' is much shorter than smooth cordgrass cv. 'Vermilion'. Mean height of 123 cm across 12 environments.

*Leaves*.—Narrow, sharply pointed, and alternately arranged. Mean leaf widths for 'LA11-103' are similar (~6.1 mm) to smooth cordgrass cv. 'Vermilion' (~6.6 mm) when measured approximately 3 mm from stem. When grown in an environment with abundant fertilization in Southern Louisiana leaves are dark green (7.5 GY 5/4).

*Flowering period*.—'LA11-103' inflorescences emerge in early summer and remain intact until late fall in Southern Louisiana when spikes shatter and disperse caryopscs.

*Panicle*.—Panicles are terminal. Numerous spikes are attached to an elongated rachis. Spikes are appressed to rachis, alternately arranged around the rachis, and consist of numerous spikelets with one floret per spikelet along one side of each spike. 'LA11-103' panicles are on average 22.2 cm long and 2.8 mm wide.

*Rhizomes*.—Rhizomes are white and hollow, fast-growing.

*Culture*.—Aquatic production in saline or fresh water. In saline production salt crystals typically form on leaf surfaces. Best growth when interlidal conditions are simulated: flooded production followed by dry production in daily or weekly intervals.

*Diseases*.—'LA11-103' has similar mean rust (caused by *Puccinia sparganioides* Ellis & Tracy) resistance as smooth cordgrass cv, 'Vermilion' at seven environments.

Growth and propagation:

*Vegetative propagation*.—From rhizomes that are approximately 2.5 to 8 cm long with at least one clum attached.

*Growth rate*.—Vigorous.

*Seed propagation*.—Not allowed for propagation of 'LA11-103'.

'LA11-103' and thirty-nine (39) additional genotypes were evaluated in experiments at Baton Rouge and Grand Terre, La., from 2000-2001. 'LA11-103' and seven (7) genotypes were selected in the fourth selection cycle. In 2002, rhizomes and stems of 'LA11-102' were harvested from experimental plots at Baton Rouge and planted into containers in controlled greenhouses. This asexual reproduction was used solely to provide material for continued experimental evaluations.

Experimental evaluations were continued from 2005-2009 at seven sites. In 2010, 'LA11-103' was identified as a superior cultivar and one hundred (100) single stems with rhizomes, which were verified using molecular markers to be genetically identical, were used to asexually propagate the variety 'LA11-103' in Plaquemines Parish, Louisiana. In 2011, rhizome and stem material were harvested and moved to Baton Rouge where asexual reproduction of rhizomes and stems has continued.

Variation in plant appearance can be caused by production conditions and does not reflect genetic differences. 'LA11-103' is genetically identical and stable when produced from rhizome material. 'LA11-103' can be definitely identified from 'Vermilion' based upon fragment size differences at ten (10) molecular markers, and from 'LA11-101' and 'LA11-102' using nine (9) molecular markers (Table 1).

TABLE 1

| Primer† | LA11-103 | Vermilion | LA11-101 | LA11-102 |
|---|---|---|---|---|
| | Fragment Size (bp) | | | |
| ESSR35 | 200 | 180 | 190 | 190 |
| ESSR58 | 400 | 400 | 400 | 420 |
| ESSR64 | 300 | 300 | 310 | 310 |
| ESSR21 | 210 | 215 | 215 | 215 |
| ESSR29 | 200 | 188 | 188 | 188 |
| ESSR66 | 140 | 140 | 145 | 145 |
| ESSR69 | 390 | 410 | 410 | 390 |
| SPAR4 | 210 | 190 | 210 | 210 |
| SPAR7 | 295 | 280 | 295 | 295 |
| SPAR8 | 200 | 180 | 185 | 185 |
| SPAR11 | 280 | 275 | 285 | 285 |
| SPAR27 | 190 | 200 | 190 | 190 |
| SPAR5 | 263 | 260 | 265 | 265 |

†ESSR sequences (Baisakh et al., 2009. *Aquat. Bot* 91:262; SPAR sequences Blum et al., 2004. *Mol. Ecol. Notes* 4: 39).

Explanation of Tests Conducted

Preliminary Field Trials:

'LA11-103' was selected from a preliminary field trial in which 400 plants were evaluated for performance in a freshwater production pond, Baton Rouge, La., in February 2000. 'LA11-103' was included in replicated trials from 2000 to 2009 in thirteen (13) environments to evaluate its performance and release potential.

Advanced Field Trials:

Advanced field trials were completed at freshwater ponds, Baton Rouge, La., and on a created marsh, Grand Terre, La., in 2001. The average plant height, spread, rust rating (*Puccinia sparganiodes*), and plant vigor were calculated based upon measurements completed every two (2) weeks starting eight (8) months after transplant and ending twelve (12) months after transplant for Baton Rouge and from three (3) to five (5) months after transplant for Grand Terre. Plant height was measured from the soil surface to the uppermost leaf tip of the plant. Plant spread was calculated by measuring the linear growth of each plant on two (2) perpendicular axes. Rust rating was measured with a 0-10 scale where 0 was no rust visible and 10 was rust covering all above-ground portions of the plant. Plant vigor was measured with a 0-10 scale where 0 was a dead plant and 10 was an extremely vigorous plant.

Elite Field Trials:

Elite field trials were completed on a created marsh at Grand Terre; on man-made marsh terraces, Cameron Parish, La., in 2003; and in freshwater rice production fields, Rayne, La., in 2005 and 2006. Plant vigor was measured at Grand Terre and Cameron Parish approximately six (6) months after transplant. Plant vigor, rust rating, plant spread, plant height, and the total number of stems per plot were measured at Rayne in 2005 and 2006, approximately five (5) months after transplant. Percent seed set and seed germination were also determined at Rayne in 2005. Percent seed set was determined on ten (10) randomly selected panicles harvested the first week of November. Each panicle was individually bagged with 4.5 cm×40 cm cellulose tubes to collect seeds that shattered prior to harvest in early December. The total number of florets and the number of florets containing seeds (filled florets) were determined using a fluorescent light box. Percent seed set was calculated as follows: [(number of filled seed/total number of florets)* 100]. Percent seed germination was determined with five (5) replicates of one hundred (100) seeds. Seeds were placed into Petri dishes containing a #4 filter paper and 8 ml of 0.05% 200 g/L carboxin and 200 g/L thiram solution. Petri dishes were sealed with parafilm to minimize evaporation and placed in an incubator at 24-26° C. and 16/8 hr light/dark for six (6) weeks and percent seed germination was calculated.

Supreme Field Trials:

Supreme field trials were evaluated at a man-made marsh terrace, Cameron Parish, La., in 2008; two (2) eroded marsh areas, Grand Chenier, La., in 2008 and 2009; and two (2) freshwater rice production fields, Rayne, La. in 2008 and 2009. Plant vigor was measured at Cameron Parish one (1) month after transplant. Plant vigor and number of stems were measured at Cameron Parish one (1) year after transplant. Plant vigor, rust rating, plant spread, plant height, and number of stems per plot were measured approximately six (6) months after transplant at Grand Chenier in 2008 and 2009. Plant vigor, rust rating, plant spread, plant height, number of stems, percent seed set, and percent seed germination were measured at Rayne in 2008 and 2009, approximately six (6) months after transplant.

EXAMPLE 1

Advanced Field Trials

In advanced field trials, 'LA11-103' was as vigorous, spread as far, and had a similar rust rating and plant height as 'Vermilion' (Table 2).

TABLE 2

| Variety | Height† (cm) | Spread ($m^2$) | Rust‡ | Vigor§ |
|---|---|---|---|---|
| | Baton Rouge, LA | | | |
| 'LA11-103' | 121.0 a | 2.2 a | 3.4 a | 7.5 a |
| 'Vermilion' | 140.0 a | 1.0 a | 3.5 a | 7.2 a |
| | Grand Terre Island, LA | | | |
| Variety | Height (cm) | Spread ($m^2$) | Rust | Vigor |
| 'LA11-103' | 87.0 a | 1.3 a | 1.8 a | 6.3 a |
| 'Vermilion' | 99.0 a | 1.2 a | 2.4 a | 6.5 a |

†Means within the same column that are followed by different letters are significantly different (t test, $p < 0.05$).
‡Rust rating was visually estimated on a scale of 0-10 (0 = no rust visible; 10 = rust covering all above-ground portions of the plant).
§Vigor was visually estimated on a scale of 0-10 (0 = dead; 10 = excellent).

EXAMPLE 2

Elite Field Trials

In elite field trials 'LA11-103' was as vigorous as 'Vermilion' at Cameron Parish, Grand Terre, and Rayne in 2006

(Table 3). It was less vigorous than 'Vermilion' at Rayne in 2005. 'LA11-103' also spread as far and had a similar rust reaction as 'Vermilion' (Table 3). 'LA11-103' had higher seed set and seed germination than 'Vermilion' and was shorter and had less stems per plot than 'Vermilion' in freshwater rice production fields (Table 3).

TABLE 3

| Variety | Vigor† | Rust‡ | Spread ($m^2$) | Height (cm) |
|---|---|---|---|---|
| Cameron Parish, 2003 | | | | |
| 'LA11-103' | 7.8 a | — | — | — |
| 'Vermilion' | 8.8 a | — | — | — |
| Grand Terre, 2003 | | | | |
| 'LA11-103' | 5.6 a | — | — | — |
| 'Vermilion' | 7.8 a | — | — | — |
| Rayne, 2005 | | | | |
| 'LA11-103' | 8.3 b | 2.3 a | 1.5 a | 146.0 b |
| 'Vermilion' | 9.7 a | 2.7 a | 2.5 a | 209.3 a |
| Rayne, 2006 | | | | |
| 'LA11-103' | 8.0 a | 3.3 a | 1.4 a | 153.3 b |
| 'Vermilion' | 9.0 a | 2.3 a | 2.6 a | 218.0 a |

| Variety | Number of Stems | Seed Set (%) | Seed Germination (%) |
|---|---|---|---|
| Cameron Parish, 2003 | | | |
| 'LA11-103' | — | — | — |
| 'Vermilion' | — | — | — |
| Grand Terre, 2003 | | | |
| 'LA11-103' | — | — | — |
| 'Vermilion' | — | — | — |
| Rayne, 2005 | | | |
| 'LA11-103' | 83.7 b | 55.0 a | 76.0 a |
| 'Vermilion' | 138.3 a | 20.7 b | 35.3 b |
| 'LA11-103' | 82.3 b | — | — |
| 'Vermilion' | 121.7 a | — | — |

†Vigor was visually estimated on a scale of 0-10 (0 = dead; 10 = excellent); Means within the same column and location followed by different letters are significantly different (t test, $p < 0.05$).
‡Rust rating was visually estimated on a scale of 0-10 (0 = no rust visible; 10 = rust covering all above-ground portions of the plant).

EXAMPLE 3

Supreme Field Trials

In supreme field trials, 'LA11-103' was more vigorous than 'Vermilion' one month after transplant on man-made marsh terraces in Cameron Parish (Table 4). 'LA11-103' was as vigorous, spread as far, and had approximately an equal number of stems per plot and rust rating as 'Vermilion' at the remaining locations (Table 4). 'LA11-103' had a higher seed set and germination rate than 'Vermilion' (Table 4). It was also shorter than 'Vermilion' in supreme field trials (Table 4).

TABLE 4

| Variety | Vigor† | Rust‡ | Spread ($m^2$) | Height (cm) |
|---|---|---|---|---|
| Cameron Parish, 2008§ | | | | |
| 'LA11-103' | 4.7 a | — | — | — |
| 'Vermilion' | 1.0 b | — | — | — |
| Cameron Parish, 2009§ | | | | |
| 'LA11-103' | 4.3 a | — | — | — |
| 'Vermilion' | 4.7 a | — | — | — |
| Grand Chenier, 2008 | | | | |
| 'LA11-103' | 7.3 a | 3.3 a | 1.5 a | 99.0 b |
| 'Vermilion' | 10.0 a | 1.3 a | 2.6 a | 164.0 a |
| Grand Chenier, 2009 | | | | |
| 'LA11-103' | 8.0 a | 3.0 a | 1.8 a | 101.0 b |
| 'Vermilion' | 9.3 a | 1.0 a | 2.5 a | 153.0 a |
| Rayne, 2008 | | | | |
| 'LA11-103' | 7.0 a | 2.7 a | 1.1 a | 123.0 b |
| 'Vermilion' | 8.7 a | 2.7 a | 2.6 a | 209.0 a |
| Rayne, 2009 | | | | |
| 'LA11-103' | 7.0 a | — | 0.9 a | 153.0 b |
| 'Vermilion' | 9.3 a | — | 1.8 a | 188.0 a |

| Variety | Number of Stems | Seed Set (%) | Seed Germination (%) |
|---|---|---|---|
| Cameron Parish, 2008§ | | | |
| 'LA11-103' | — | — | — |
| 'Vermilion' | — | — | — |
| Cameron Parish, 2009§ | | | |
| 'LA11-103' | 11.0 a | — | — |
| 'Vermilion' | 16.0 a | — | — |
| Grand Chenier, 2008 | | | |
| 'LA11-103' | 78.0 a | — | — |
| 'Vermilion' | 92.7 a | — | — |
| Grand Chenier, 2009 | | | |
| 'LA11-103' | 71.0 a | — | — |
| 'Vermilion' | 92.3 a | — | — |
| Rayne, 2008 | | | |
| 'LA11-103' | 63.0 a | 63.0 a | 76.3 a |
| 'Vermilion' | 102.7 a | 27.3 b | 38.0 b |
| Rayne, 2009 | | | |
| 'LA11-103' | 66.0 a | 58.3 a | 72.0 a |
| 'Vermilion' | 107.0 a | 21.3 b | 40.0 b |

†Vigor was visually estimated on a scale of 0-10 (0 = dead; 10 = excellent); Means within the same column and location followed by different letters are significantly different (t test, $p < 0.05$).
‡Rust rating was visually estimated on a scale of 0-10 (0 = no rust visible; 10 = rust covering all above-ground portions of the plant).
§Cameron Parish was established in 2008 and evaluated in 2008 one (1) month after transplant and in 2009 one (1) year after transplant.

We claim:

1. A new and distinct plant variety of *Spartina alterniflora* named 'LA11-103' as described and illustrated in the specification herein.

* * * * *